(12) United States Patent
Sheridan et al.

(10) Patent No.: US 9,848,837 B2
(45) Date of Patent: Dec. 26, 2017

(54) IMAGING SYSTEM ROTATING COMPONENT ALIGNMENT WITH ISO-CENTER

(71) Applicant: KONINKLIJKE PHILIPS N.V., Eindhoven (NL)

(72) Inventors: Rosemarie Sheridan, Mayfield Village, OH (US); Samuel Andreas Johanson, Cleveland Heights, OH (US); Joshua Samuel Sapp, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 14/888,948

(22) PCT Filed: Apr. 23, 2014

(86) PCT No.: PCT/IB2014/060921
§ 371 (c)(1),
(2) Date: Nov. 4, 2015

(87) PCT Pub. No.: WO2014/181207
PCT Pub. Date: Nov. 13, 2014

(65) Prior Publication Data
US 2016/0073973 A1 Mar. 17, 2016

Related U.S. Application Data (60) Provisional application No. 61/819,837, filed on May 6, 2013.

(51) Int. Cl.
A61B 6/03 (2006.01)
A61B 6/00 (2006.01)

(52) U.S. Cl.
CPC .............. *A61B 6/035* (2013.01); *A61B 6/037* (2013.01); *A61B 6/4429* (2013.01);
(Continued)

(58) Field of Classification Search
CPC .. A61B 6/00; A61B 6/03; A61B 6/035; A61B 6/037; A61B 6/587
(Continued)

(56) References Cited

U.S. PATENT DOCUMENTS 4,459,485 A 7/1984 Span
4,709,559 A 12/1987 Dotzauer et al.
(Continued)

FOREIGN PATENT DOCUMENTS

DE 102011081257 2/2013
EP 0109206 5/1984
(Continued)

*Primary Examiner* — Jurie Yun (57) ABSTRACT

An imaging system (100) includes an annular bearing (404) with an iso-center (406). The annular bearing includes a stationary side (404₁) and a rotatable side (404₂) with at least one alignment feature (420). The imaging system further includes a rotating gantry (410) mechanically coupled to the rotatable side. The imaging system further includes an imaging component (412, 416, 418). The imaging components includes at least one complementary alignment feature (602, 804) that is complementary to the at least one alignment feature (420, 802, 1200) of the rotatable side. The rotating gantry is between the imaging component and the rotatable side, and the imaging component is aligned with the iso-center through the at least one alignment feature and the at least one complementary alignment feature.

19 Claims, 6 Drawing Sheets

(52) U.S. Cl.
CPC ............ *A61B 6/4435* (2013.01); *A61B 6/587* (2013.01); *A61B 6/4291* (2013.01)

(58) Field of Classification Search
USPC ........................................ 378/4, 15, 19, 205
See application file for complete search history.

(56) References Cited

U.S. PATENT DOCUMENTS

| | | |
|---|---|---|
| 6,337,894 B1 | 1/2002 | Tybinkowski et al. |
| 6,404,845 B1 | 6/2002 | Sharpless et al. |
| 2004/0057556 A1 | 3/2004 | Luhta et al. |
| 2009/0168948 A1 | 7/2009 | Luo et al. |
| 2010/0195949 A1 | 8/2010 | Yagi et al. |
| 2011/0194669 A1 | 8/2011 | Tremaine et al. |
| 2012/0027163 A1 | 2/2012 | Mochitate |
| 2012/0027183 A1 | 2/2012 | Sharpless et al. |

FOREIGN PATENT DOCUMENTS

| | | |
|---|---|---|
| JP | 58182712 | 12/1983 |
| WO | 99/19882 | 4/1999 |
| WO | 2013/031684 | 3/2013 |

IMAGING SYSTEM ROTATING COMPONENT ALIGNMENT WITH ISO-CENTER

This application is the U.S. National Phase application under 35 U.S.C. §371 of International Application No. PCT/IB2014/060921, filed on Apr. 23, 2014, which claims the benefit of U.S. Patent Application No. 61/819,837, filed on May 6, 2013. These applications are hereby incorporated by reference herein.

The following generally relates to an imaging system and more particularly to aligning one or more rotating components with respect to iso-center of the imaging system, and is described with particular application to computed tomography (CT). However, the following is also amenable to other modalities such a positron emission tomography (PET), single photon emission computed tomography (SPECT), and/or other imaging modalities.

A CT scanner generally includes a stationary frame and a rotating frame, which is rotatably supported on the stationary frame via a bearing or the like. An x-ray tube with a focal spot and a detection system are mounted to and rotate with the rotating frame, with the x-ray tube being located opposite the detection system, across an examination region.

The focal spot emits radiation which is collimated by a collimator, producing a radiation beam that traverses the examination region and a subject or object therein. The detection system detects radiation that traverses the examination region and generates projection data indicative thereof. A reconstructor reconstructs the projection data, generating volumetric image data indicative thereof.

Figure 1:
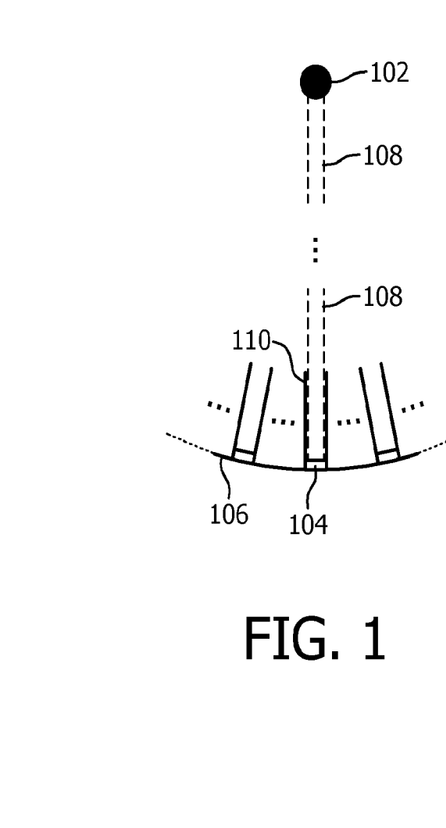
FIG. 1 schematically illustrates accurate alignment of a detector pixel/anti-scatter grid assembly and a focal spot.
Figure 2:
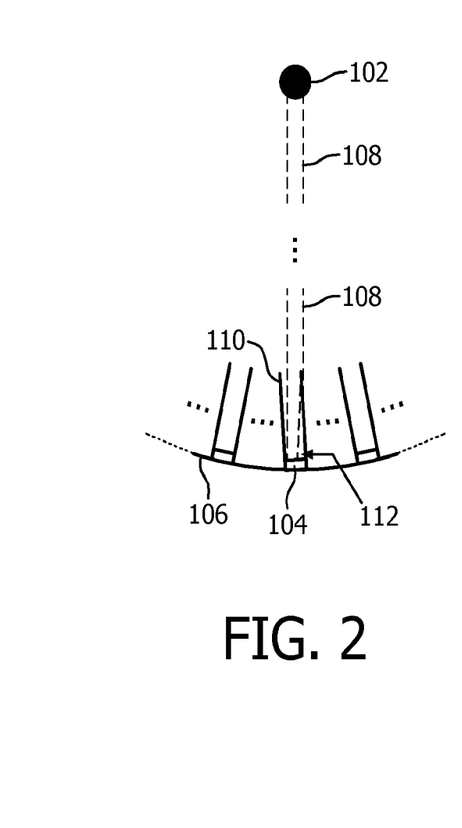
FIG. 2 schematically illustrates misalignment between the detector pixel/anti-scatter grid assembly and the focal spot.

The alignment of the focal spot and the detection system can impact image quality. For example, if the alignment is off, then some of the radiation that should otherwise impinge a detector pixel of the detection system may not. In one instance, this results in shadowing, which introduces ring artifact into the resulting reconstructed image data. This is shown in FIGS. 1 and 2. In FIG. 1, with accurate spatial alignment of a focal spot 102 and a detector pixel 104/anti-scatter grid 110 assembly of a detector array 106, radiation 108 traversing a path from the focal spot 102 through the anti-scatter grid 110 impinges the detector pixel 104. In FIG. 2, however, with misalignment of the focal spot 102 and the detector pixel 104/anti-scatter grid 110 assembly, a sub-portion of the radiation 108 is attenuated by the anti-scatter grid 110 such that a sub-portion 112 of the detector pixel 104 receives none of the radiation 108, or is shadowed.

Figure 3:
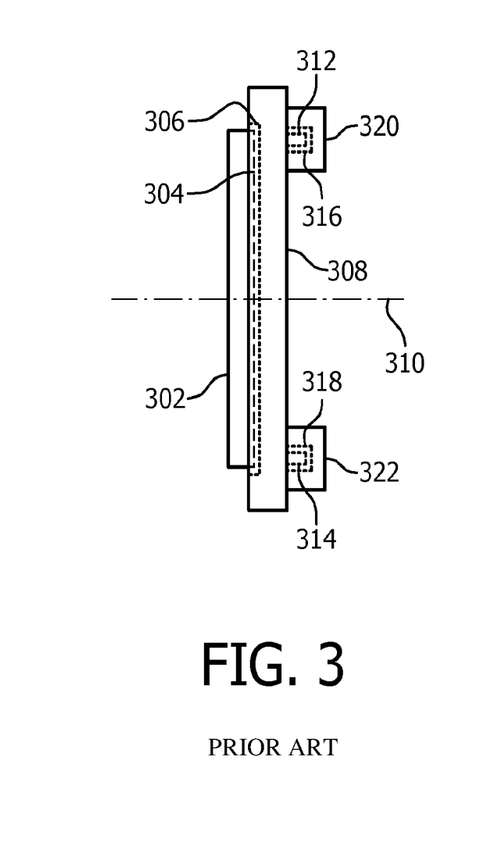
FIG. 3 schematically illustrates a prior art example of couplings aligning the detection system with the rotating gantry and the rotating gantry with the bearing.

Accurate alignment of the focal spot and the detection system has been achieved through tight tolerances on the interfaces between different sub-components of the CT scanner. By way of non-limiting example, as shown in FIG. 3, a bearing 302 is machined with a protruding concentric circle or cylinder 304 that interfaces with a complementary recess 306 on a rotating frame 308, approximately aligning the rotating frame 308 with respect to iso-center 310, or the center of the bearing 302. The rotating frame 308 has alignment pins 312 and 314 that engage complementary recesses 316 and 318 of an x-ray tube 320 and a detection system 322, approximately aligning the x-ray tube 320 and the detection system 322 with each other and the rotating frame 308. With this approach, the x-ray tube 320 and the detection system 322 are aligned with the rotating frame 308, which is aligned with the bearing 302.

For accurate alignment, with this approach, the different components have tightly controlled tolerances, which align their critical features to their matching alignment features. Unfortunately, this approach leads to higher costs for at least the bearing, the rotating frame, and the detection system due at least to the machining cost added to each of these components. In addition, with manufacturing limitations and tolerance stack up, there may still be an inherent inaccuracy in this approach, which cannot be accounted for or removed. This inaccuracy may not only lead to reduced image quality but may also lead to radiation dose inefficiencies since all of the x-rays traversing the subject or object being scanned may not be detected by the detection system. Therefore, there is an unresolved need for other approaches for aligning certain components of an imaging system with iso-center. This includes imaging systems with ball, air, and/or other types of bearings.

Aspects described herein address the above-referenced problems and others.

The following describes an imaging system with more accurate placement and alignment of at least the detection system with respect to iso-center and reduced machining tolerances on certain components. In one instance, this is achieved by removing the rotating gantry from the tolerance chain and relying on the bearing to accurately position the detection system.

In one aspect, an imaging system includes an annular bearing with an iso-center. The annular bearing includes a stationary side and a rotatable side with at least one alignment feature. The imaging system further includes a rotating gantry mechanically coupled to the rotatable side. The imaging system further includes an imaging component. The imaging components includes at least one complementary alignment feature that is complementary to the at least one alignment feature of the rotatable side. The rotating gantry is between the imaging component and the rotatable side, and the imaging component is aligned with the iso-center through the at least one alignment feature and the at least one complementary alignment feature.

In another aspect, a method includes providing at least a sub-portion of an imaging system in which at least a detection system of the sub-portion is spatially aligned with and rotates with a rotating portion of an annual bearing of the sub-portion such that the detection system is spatially aligned with an iso-center of the rotating portion. A rotating gantry is between the detection system and the rotatable portion of the annual bearing.

In another aspect, an imaging system includes an annular bearing with an iso-center. The annular bearing includes a stationary side and a rotatable side with at least one alignment feature. The imaging system further includes a rotating gantry mechanically coupled to the rotatable side. The imaging system further includes an imaging component. The imaging components includes at least one complementary alignment feature that is complementary to the at least one alignment feature of the rotatable side. The imaging system further includes an alignment device. The rotating gantry is between the imaging component and the rotatable side. The imaging component is automatically spatially aligned with the iso-center when the alignment device is installed concurrently in both the at least one alignment feature and the at least one complementary alignment feature.

The invention may take form in various components and arrangements of components, and in various steps and arrangements of steps. The drawings are only for purposes of illustrating the preferred embodiments and are not to be construed as limiting the invention.

Figure 4:
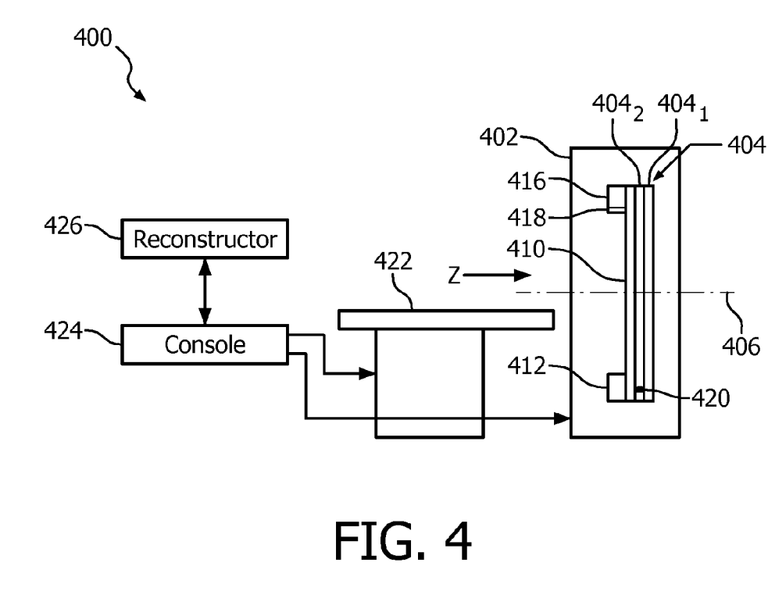
FIG. 4 schematically illustrates an example imaging system in which at least the detection system is aligned with the bearing and not the rotating frame.
Figure 5:
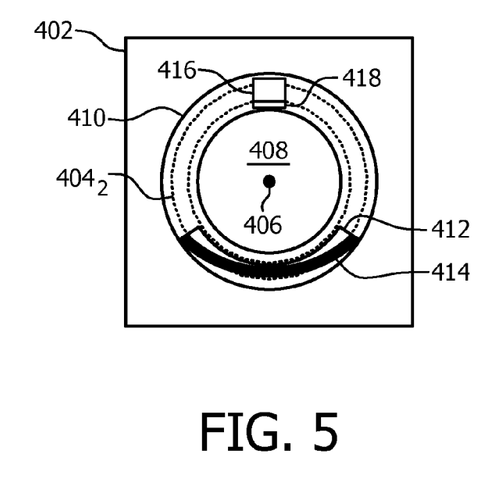
FIG. 5 schematically illustrates a front view of a portion of the imaging system of FIG. 4.

Referring to FIGS. 4 and 5, an imaging system 400 such as a computed tomography (CT) scanner, is illustrated. FIG. 4 illustrates a side view of the imaging system 400, and FIG. 5 illustrates a sub-portion of the imaging system 400, looking into the imaging system 400. The imaging system 400 includes a stationary gantry 402, which is generally stationary in that it may be configured to tilt.

An annular bearing 404 includes a first bearing sub-portion $404_1$ and a second bearing sub-portion $404_2$, and defines an iso-center 406 (or a center of the annular bearing 404). The first bearing sub-portion $404_1$ is mechanically fixed at a static location within the stationary gantry 402. The second bearing sub-portion $404_2$ is rotatably coupled to the first bearing sub-portion $404_1$ and rotates an examination region 408 about a longitudinal or z-axis. The bearing 404 can be a ball bearing, an air bearing, and/or other bearing.

A rotating gantry 410 is mounted to the second bearing sub-portion $404_2$. A detection system 412, including a radiation sensitive detector array 414, is mounted to the second bearing sub-portion $404_2$ and/or the rotating gantry 410. A radiation source 416 and a collimator 418 are located opposite the detection system 412, across from the examination region 408. The radiation source 416 emits radiation that is collimated by the collimator 418 and detected by the detection system 412, which generates projection data indicative thereof As described in greater detail below, the second bearing sub-portion $404_2$ includes at least one alignment feature 420, which is used to spatially align at least one component (e.g., the detection system 412, the radiation source 416, the collimator 418 and/or other component(s)) with respect to the iso-center 406. For explanatory purposes, clarity, and sake of brevity, one alignment feature 420 is shown in FIG. 4 in the second bearing sub-portion $404_2$. However, this example is not limiting, and the alignment feature 420 may include multiple alignment features.

Generally, the alignment feature 420 provides a mechanical stop such that when a complementary alignment feature of a component (e.g., the detection system 412, the radiation source 416, etc.) being aligned with the second sub-portion of the bearing $404_2$ and the iso-center 406 engages the alignment feature 420, the component is not free to translates or rotate, and is accurately held at a pre-determined alignment position. At this position, the component can be affixed to the second sub-portion of the bearing $404_2$ and/or other structure of the system 400. It is to be appreciated that the feature 420 on the second bearing sub-portion $404_2$ allows for aligning a component with the bearing 404, and not the rotating gantry 410, which allows for removing the rotating gantry 410 from the tolerance stack up chain. In this way there is substantially less inherent misalignment, which may become more critical as the detection system pixel size becomes smaller. In addition, removing the tight machining tolerances on the rotating gantry 410 may decrease the cost of the rotating gantry 410 and the overall system by allowing for the use of components with less inherent accuracy.

A patient support 422, such as a couch, supports an object or subject in the examination region 408. The support 422 is configured to move the object or subject for loading, scanning, and/or unloading the object or subject. A computing system or computer serves as an operator console 424. The console 424 allows an operator to control operation of the system 400. A reconstructor 426 reconstructs the projection data and generates reconstructed volumetric image data indicative thereof.

Figure 6:
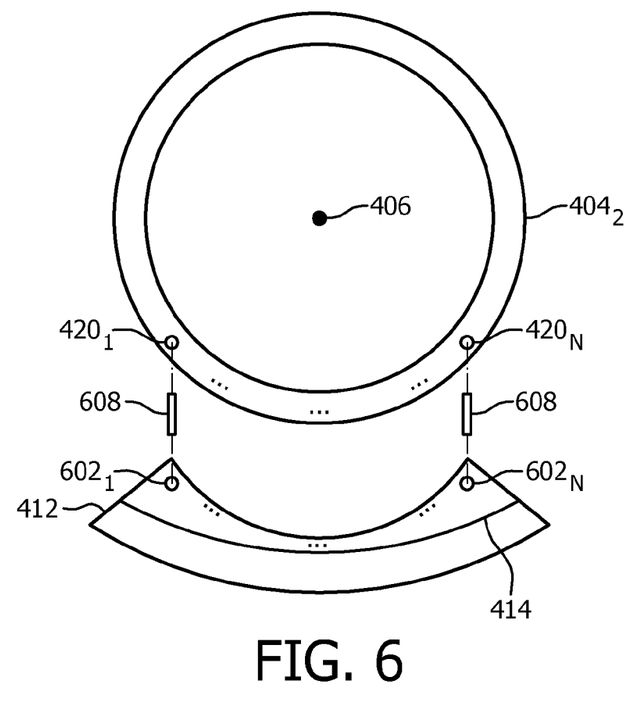
FIG. 6 schematically illustrates an example with at least two features on the bearing used to align and mount the detection system to the bearing.
Figure 7:
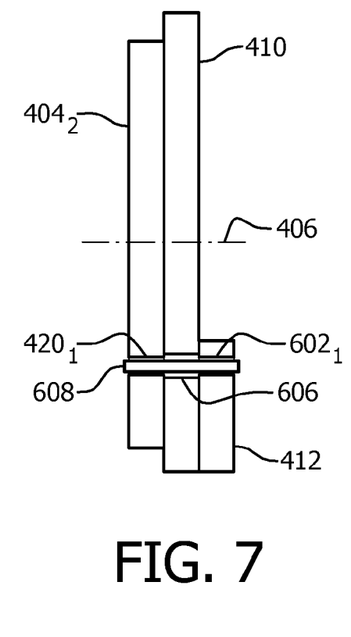
FIG. 7 illustrates a side view of the example of FIG. 6.

FIGS. 6 and 7 illustrate a non-limiting example of the at least one alignment feature 420 in connection with the detection system 412. FIG. 6 shows a front view looking into the second sub-portion of the bearing $404_2$, and FIG. 7 shows a side view. For sake of clarity, in FIG. 6, the rotating gantry 410 is not shown and the second sub-portion of the bearing $404_2$ and the detection system 412 are shown in an exploded view in which these components are separated.

In this embodiment, the alignment feature 420 includes N sub-alignment features $420_1, \ldots, 420_N$. In the illustrated embodiment, a first sub-alignment feature $420_1$ is located on one side of the iso-center 406 and a second sub-alignment feature $420_N$ is located on an opposing side of the iso-center 406. In a variation, the sub-alignment features $420_1$ and $420_N$ are located on the same side of the iso-center 406. The illustrated location is not limiting.

The detection system 412 includes complementary alignment features, including a first complementary alignment feature $602_1$ and a second complementary alignment feature $602_N$. In the illustrated examples, the first and second sub-alignment features $420_1$ and $420_N$ and the first and second complementary alignment features $602_1$ and $602_N$ are accurately machined holes, which spatially align with each other, and when aligned with each other, align the detection system 412 with the iso-center 406.

As shown in FIG. 7, the rotating gantry 410 includes a material free passage 606 arranged to extends between the accurately machined holes $420_1, 420_N, 602_1$ and $602_N$ when the rotating gantry 410 and the detection system 412 are installed on the second sub-portion of the bearing $404_2$. The material free passage 606 need not be accurately machined like the holes $420_1, 420_N, 602_1$ and $602_N$. In the illustrated embodiment, the passage 606 is shown with a slightly larger diameter relative to the holes $420_1, 420_N, 602_1$ and $602_N$, but could have a same diameter.

An alignment device 608, when installed in the machined holes $420_1, 420_N, 602_1$ and $602_N$ aligns the detection system 412 with the iso-center 406, or center of the second portion of the bearing $404_2$. The illustrated device 602 includes a fastener such as a screw, a bolt, a rivet, etc., which mechanically engages the holes $420_1$, $420_N$, $602_1$ and $602_N$ and physically fastens the second sub-portion of the bearing $404_2$ and the detection system 412 together. The device 608 may install from the second portion of the bearing $404_2$ or the detection system 412 side.

In FIG. 7, the device 608 is shown protruding out of the second portion of the bearing $404_2$ and the detection system 412. In another embodiment, the device 608 only protrudes from one of or none of the second portion of the bearing $404_2$ and the detection system 412. In another embodiment, the device 608 is part of one of the second portion of the bearing $404_2$ and the detection system 412 and is not removable. In another example, the device 608 may be "C" or "U" shaped and clamp around the outside of the components and engage the alignment features.

Figure 8:
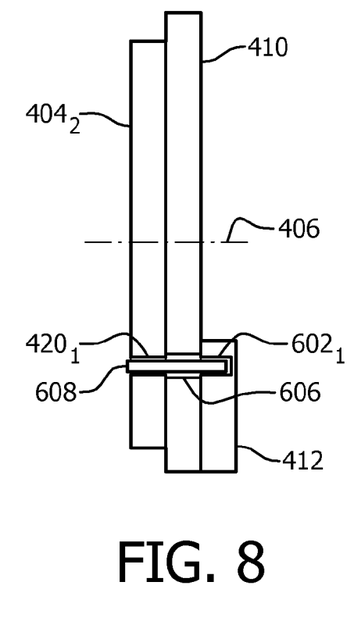
FIG. 8 illustrates a variation of FIG. 7 in which the alignment device installs from the bearing side.
Figure 9:
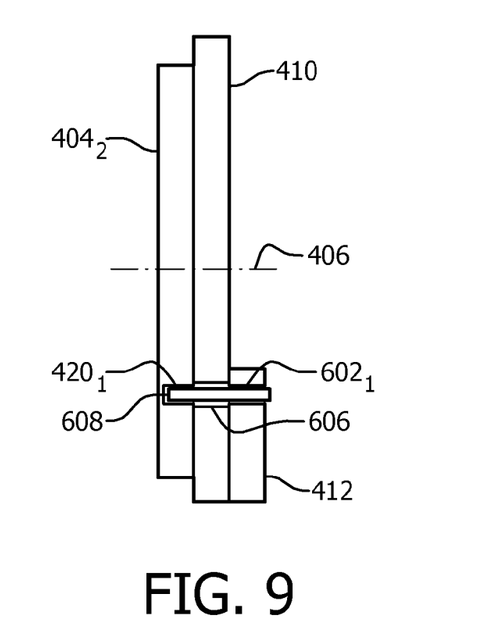
FIG. 9 illustrates another variation of FIG. 7 in which the alignment device installs from the detection system side.

FIG. 8 shows a variation in which the device 608 installs from the second portion of the bearing $404_2$ side and does not extend completely through the detection system 412 side. FIG. 9 shows a variation in which the device 608 installs from the detection system 412 side and does not extend completely through the second portion of the bearing $404_2$ side. Other configurations are also contemplated herein. For example, the device 608 may be curved or irregular in shape and/or the alignment features may align with each other along angle instead of the illustrated horizontal.

Returning to FIGS. 6 and 7, with this embodiment, the rotating gantry 410 need not support the detection system 412 (although it could) and may only support the radiation source 416, the collimator 418, and/or other components such as a high voltage unit, a control unit, counterweights, support electronics for the components, etc. This allows for a smaller and/or lighter rotating gantry 410, and components supported by the rotating gantry 410 could have reduced accuracy requirements, leading to a rotating gantry that would be easier to manufacture and cost less.

Figure 10:
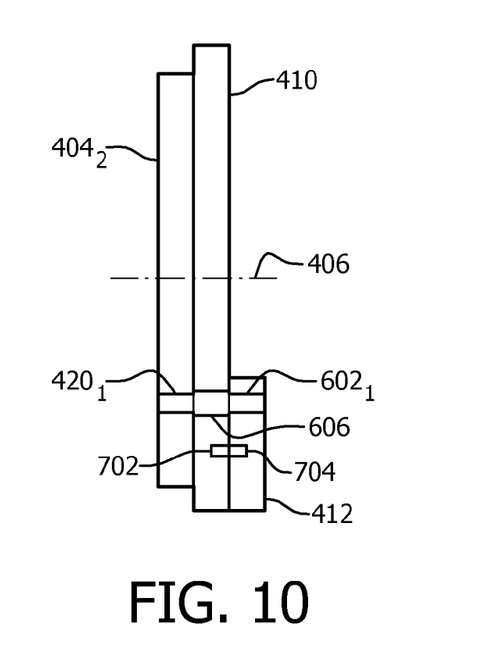
FIG. 10 illustrates a variation of FIG. 7 in which the at least two features are only used to align the detection system.

FIG. 10 illustrates a variation of FIG. 7 in which the two or more features $420_1$ and $420_N$ and the device 608 only align the detection system 412, and at least one mounting feature 702 of the rotating gantry 410 mounts the detection system 412 to the rotating gantry 410 via a complementary mounting feature 704 of the detection system 412 to affix the detection system 412 to the rotating gantry 410.

With this variation, the detection system 412 would first be aligned to the second sub-portion of the bearing $404_2$ using the holes $420_1$, $420_N$, $602_1$ and $602_N$ and the device 608. Then, the detection system 412 is mechanically coupled through the mounting features 702 and 704 (e.g., with a bolt, a screw, a rivet, etc.) to the rotating gantry 410. In this embodiment, the device 608 is a pin, rod, or the like. The pins or rods can remain in the holes $420_1$, $420_N$, $602_1$ and $602_N$ or be removed (as shown).

The latter may facilitate achieving a more uniform bearing load, which may facilitate preserving bearing life. With this embodiment, since the components are aligned to each other accurately through the at least two features $420_1$ and $420_2$, the mounting features 702 and 704 can be less accurate, relative to a configuration in which the features 702 and 704 are also used to align the components. The rotating gantry 410 is of course mechanically mounted to the second sub-portion of the bearing $404_2$.

In a variation, the detection system 412 can be mounted to both the second sub-portion of the bearing $404_2$ and the rotating gantry 410. In this variation and/or in one or more other embodiments disclosed herein, the detection system 412 can be mounted to the second sub-portion of the bearing $404_2$ through a mechanism other that the alignment feature 420, or through the alignment feature 420 and at least one additional mechanism.

Figure 11:
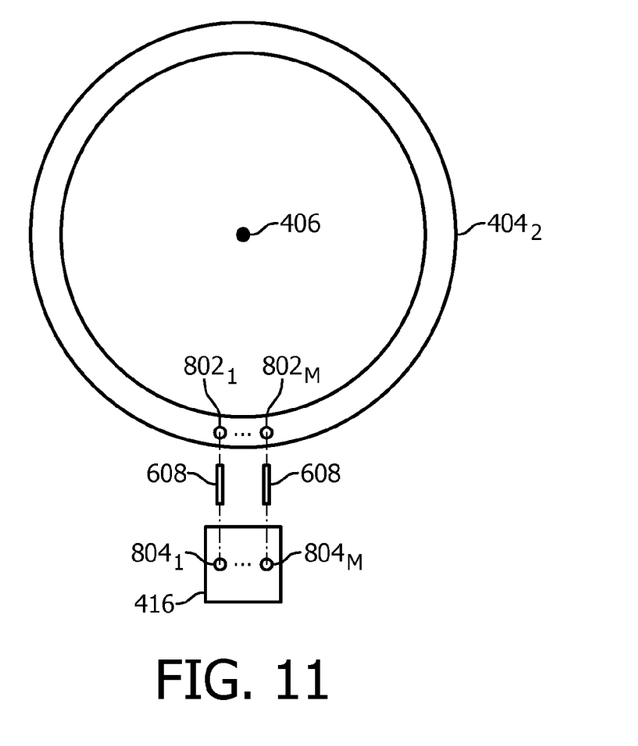
FIG. 11 illustrates a variation of FIG. 6 in which the at least two features are used to at least align the radiation source.

FIG. 11 illustrates an embodiment in which the second sub-portion of the bearing $404_2$ includes M alignment features $802_1$, . . . , $802_M$ for aligning the radiation source 416 (and/or optionally the collimator 418) with respect to the iso-center 406. In this embodiment, the radiation source 416 includes complementary alignment features $804_1$, . . . , $804_M$. In one instance, the alignment features $802_1$, $802_M$, $804_1$, $804_M$ are similar to the sub-alignment features $420_1$, $420_N$, $602_1$ and $602_N$ (FIGS. 6-10) with respect to aligning and/or mounting a component.

In another variation, FIGS. 6 and 11 can be combined such that more than one component (e.g., the detection system 412, the radiation source 416, and/or the collimator 418) is aligned via the alignment feature 420 of the second sub-portion of the bearing $404_2$. In yet another variation, another set of alignment features can be used for the collimator 418 and/or other component.

Figure 12:
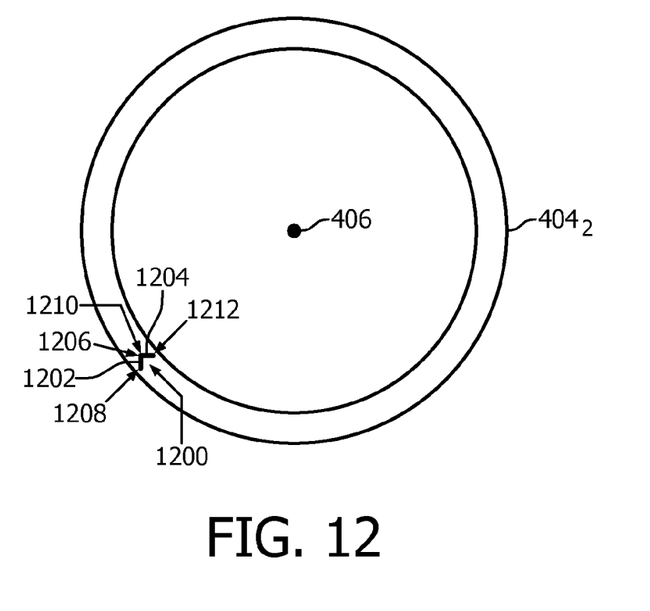
FIG. 12 illustrates a variation in which the at least one alignment feature includes a single alignment feature.

FIG. 12 illustrates a variation in which the at least one alignment feature 420 includes a single alignment feature 1200. The component being aligned is not shown. The single alignment feature 1200 may protrude from the second sub-portion of the bearing $404_2$, be a recess in the second sub-portion of the bearing $404_2$, include both protruding and recess portions, and/or otherwise be configured.

The feature 1200 includes a first elongate member 1202 that extends horizontally and a second elongate member 1204 that extends vertically (with reference to the illustrated orientation). The first member 1202 has a first end 1206 and a second end 1208, and the second member 1204 has a first end 1210 and a second end 1212. In FIG. 12, the first end 1206 of the first member 1202 is also the first end 1210 of the second member 1204.

As discussed herein, the alignment feature 1200 provides a mechanical stop such that when a complementary feature of a component (e.g., the detection system 412, the radiation source 416, etc.) being aligned with the second sub-portion of the bearing $404_2$ and the iso-center 406 engages the alignment feature 1200, the component is not free to translates or rotate, but maintained at a particular pre-determined location. In this example, the member 1202 and 1204, in combination, inhibit translation and rotation, when engages with complementary members of a component being aligned with the iso-center 406.

It is to be understood that the geometry of the illustrated single alignment feature 1200 is not limiting. For example, in other instances the members 1202 and 1204 may be curved, irregular, etc. Furthermore, the single alignment feature 1200 may include more than two members.

Figure 13:
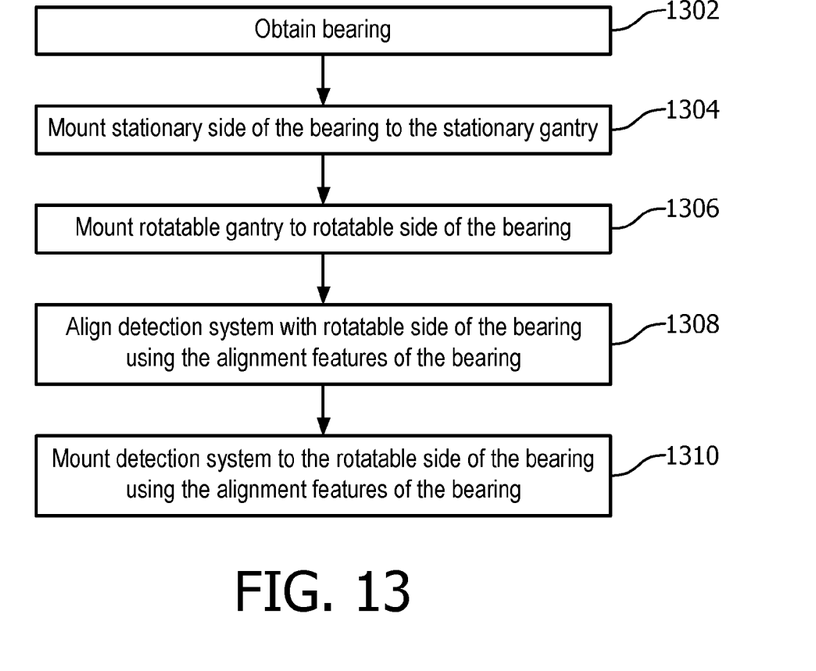
FIG. 13 illustrates a method in which at the detection system is aligned and mounted to the bearing.
Figure 14:
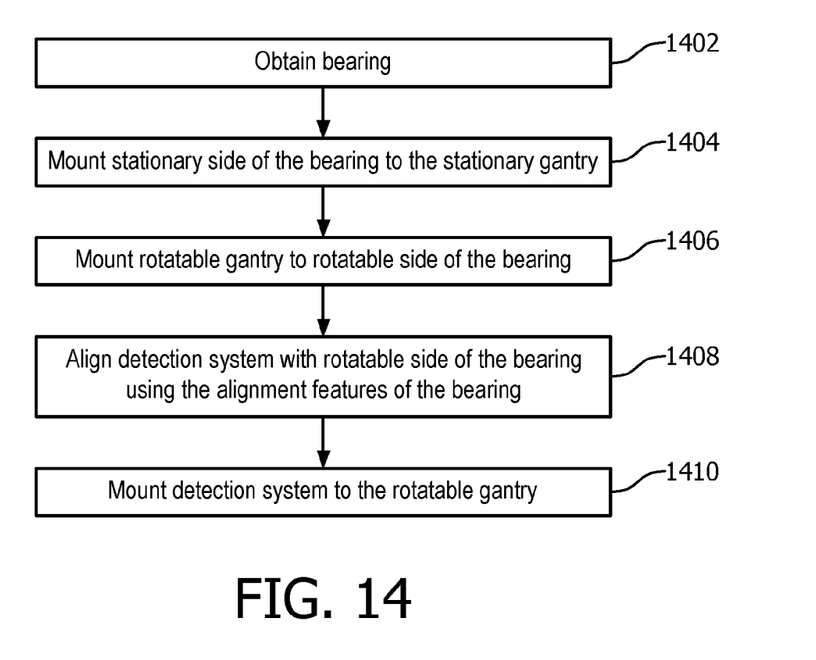
FIG. 14 illustrates a method in which at the detection system is aligned to the bearing and mounted to the rotating frame.

FIGS. 13 and 14 illustrate methods in accordance with the description herein.

It is to be appreciated that the ordering of the acts is not limiting. As such, other orderings are contemplated herein. In addition, one or more acts may be omitted and/or one or more additional acts may be included.

FIG. 13 illustrates a method in which at the detection system is aligned and mounted to the bearing.

At 1302, a bearing for a rotating gantry of an imaging system is obtained.

At 1304, the bearing is mounted to a stationary portion frame of the imaging system. The bearing includes a stationary portion and a rotatable portion.

At 1306, a rotatable frame is mounted to the rotatable portion of the bearing.

At 1308, a detection system is aligned with iso-center of the bearing via alignment features of the bearing and complementary alignment features of the detection system. One or more other components can also be aligned as such.

At 1310, the detection system is mounted to the bearing via the alignment features and the complementary alignment features.

FIG. 14 illustrates a method in which at the detection system is aligned to the bearing and mounted to the rotating frame.

At 1402, a bearing for a rotating gantry of an imaging system is obtained.

At 1404, the bearing is mounted to a stationary portion frame of the imaging system. The bearing includes a stationary portion and a rotatable portion.

At 1406, a rotatable frame is mounted to the rotatable portion of the bearing.

At 1408, a detection system is aligned with iso-center of the bearing via alignment features of the bearing and complementary alignment features of the detection system. One or more other components can also be aligned as such.

At 1410, the detection system is mounted to the rotating frame.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   an annular bearing with an iso-center, the annular bearing including:
      a stationary side; and
      a rotatable side with at least one alignment feature;
   a rotating gantry mechanically coupled to the rotatable side; and
   an imaging component, including:
      at least one complementary alignment feature that is complementary to the at least one alignment feature of the rotatable side,
   wherein the rotating gantry is between the imaging component and the rotatable side, and the imaging component is aligned with the iso-center through the at least one alignment feature and the at least one complementary alignment feature.

2. The imaging system of claim 1, wherein the imaging component is not mechanically fastened to the rotating gantry.

3. The imaging system of claim 1, wherein the imaging component is mechanically fastened to the rotatable side.

4. The imaging system of claim 3, wherein the imaging component is fastened through the at least one alignment feature.

5. The imaging system of claim 4, further comprising:
   an alignment device, wherein the imaging component is aligned and fastened via the alignment device, which physically engages both the at least one alignment feature and the at least one complementary alignment feature.

6. The imaging system of claim 5, wherein the alignment device includes a screw or a bolt.

7. The imaging system of claim 5, wherein the alignment device includes at least two sub-alignment devices.

8. The imaging system of claim 5, wherein the alignment device includes a single alignment device.

9. The imaging system of claim 1, further comprising:
   an alignment device, wherein the alignment device extends through both the at least one alignment feature and the at least one complementary alignment feature to align the rotating gantry and the imaging component.

10. The imaging system of claim 9, wherein the imaging component is mechanically fastened to the rotating gantry.

11. The imaging system of claim 10, wherein the alignment device remains in the at least one alignment feature and the at least one complementary alignment feature to align the rotating gantry and the imaging component after the imaging component is mechanically fastened to the rotating gantry.

12. The imaging system of claim 10, wherein the alignment device is removed from the at least one alignment feature and the at least one complementary alignment feature to align the rotating gantry and the imaging component after the imaging component is mechanically fastened to the rotating gantry.

13. The imaging system of claim 1, wherein the imaging component includes at least one of a detection system, a radiation source or a collimator.

14. The imaging system of claim 1, wherein the alignment feature provides a mechanical stop such that when the complementary alignment feature is held aligned therewith, the imaging component is held aligned with the iso-center and is inhibited from translating and rotating.

15. A method, comprising:
   providing at least a sub-portion of an imaging system in which at least a detection system of the sub-portion is spatially aligned with and rotates with a rotating portion of an annular bearing of the sub-portion such that the detection system is spatially aligned with an iso-center of the rotating portion, and wherein a rotating gantry of the sub-portion is between the detection system and the rotating portion, and the detection system is automatically spatially aligned with the iso-center when the detection system is fastened to the rotating portion through a fastening device.

16. The method of claim 15, wherein the detection system is not fastened to the rotating gantry.

17. The method of claim 15, wherein the detection system is also fastened to the rotating gantry.

18. The method of claim 15, wherein the rotating gantry does not affect the alignment of the detection system and the rotating portion.

19. An imaging system, comprising:
   an annular bearing with an iso-center, the annular bearing including:
      a stationary side; and
      a rotatable side with at least one alignment feature;
   a rotating gantry mechanically coupled to the rotatable side;
   an imaging component, including:
      at least one complementary alignment feature that is complementary to the at least one alignment feature of the rotatable side; and
   an alignment device,
   wherein the rotating gantry is between the imaging component and the rotatable side, and the imaging component is automatically spatially aligned with the iso-center when the alignment device is installed concurrently in both the at least one alignment feature and the at least one complementary alignment feature.

* * * * *